United States Patent [19]

Zimmermann

[11] 4,218,809
[45] Aug. 26, 1980

[54] HINGE JOINT

[75] Inventor: Josef Zimmermann, Sulzbach, Fed. Rep. of Germany

[73] Assignee: Hoechst Aktiengesellschaft, Frankfurt am Main, Fed. Rep. of Germany

[21] Appl. No.: 954,193

[22] Filed: Oct. 24, 1978

[30] Foreign Application Priority Data

Oct. 26, 1977 [DE] Fed. Rep. of Germany ....... 2747926

[51] Int. Cl.² .............................................. E05D 1/04
[52] U.S. Cl. ...................................... 16/178; 403/117
[58] Field of Search ................. 16/178, 172, 191, 179, 16/135, 128 R; 285/DIG. 8; 403/117, 119, 160, 112, 113, 91, 98

[56] References Cited

U.S. PATENT DOCUMENTS 3,256,553  6/1966  Schnur .................................... 16/178
3,256,640  6/1966  Schnur ................................ 16/178 X
3,359,594  12/1967  Pastoor ................................... 16/178
3,717,902  2/1973  Savenije .............................. 16/178 X Primary Examiner—C. J. Husar
Assistant Examiner—Moshe I. Cohen
Attorney, Agent, or Firm—Curtis, Morris & Safford

[57] ABSTRACT

In a hinge joint having compact hinge halves and porous fixing plugs (1, 2), the hinge halves are provided with recesses (26) and (27), and linked in an articulated manner and guided by at least one ring (3) and (4), respectively. The ring(s) (3, 4) run in grooves (9, 10) which are arranged concentrically to the rotation axis of the joint.

For use of the hinge joint in the medical field, it may be advantageous that the fixing plugs (1, 2) have a microporous structure and the rings (3, 4) are linked to covers (29) via bridges (28).

7 Claims, 6 Drawing Figures

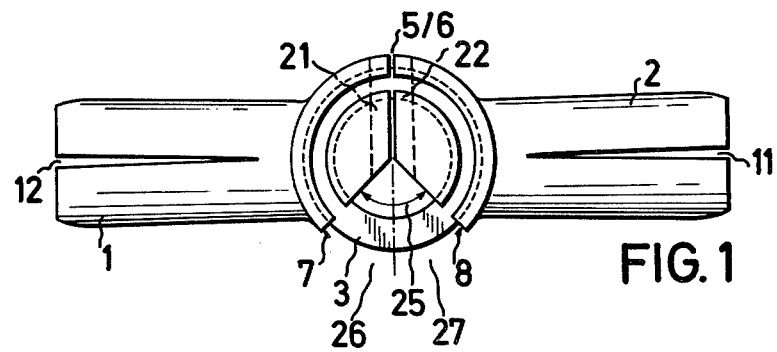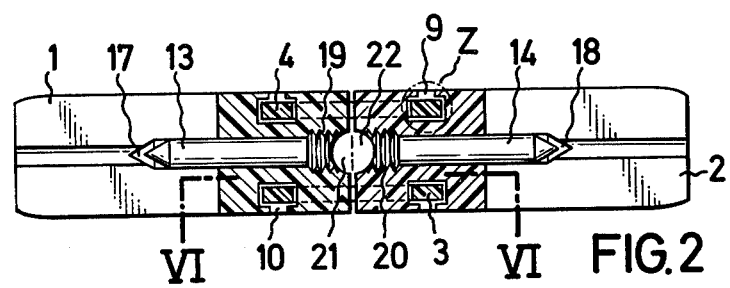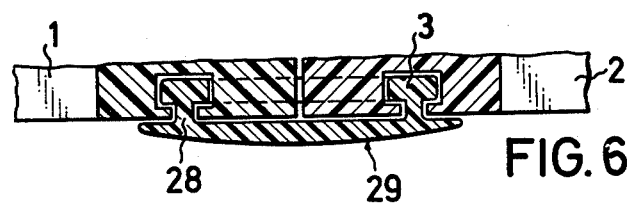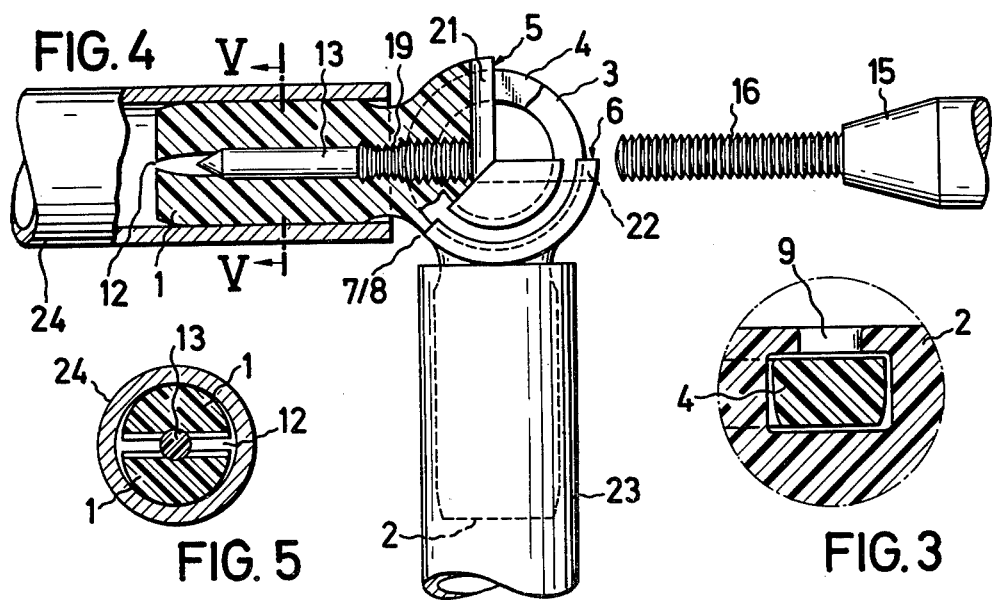

HINGE JOINT

Subject of the present invention is a hinge joint, especially a hinge joint with compact hinge halves and porous fixing plugs.

It is the object of the present invention to provide a hinge joint of the above kind, where the halves of the hinge are linked in an articulated manner neither by pins nor film hinges. Furthermore, the hinge joint must have a certain mobility transverse and parallel to the rotation axis.

This object is achieved by a hinge joint wherein the hinge halves are provided with recesses and linked in an articulated manner and guided by at least one, preferably two rings, which run in corresponding grooves arranged concentrically to the rotation axis of the hinge.

The recesses in the hinge halves may be chosen in accordance with the intended swivelling range of the hinge joint. However, 35% of each ring at least should be guided in the grooves of the hinge halves, which grooves may be undercut in order to secure the rings. By adjusting a defined clearance of the guide rings, a certain mobility of the hinge joint transverse and parallel to the rotation axis can be obtained, which is advantageous for compensating possible errors in alignment of the hinge parts to be linked. The hinge halves are provided with fixing elements arranged radially of the rotation axis, which elements may be straps when plane pieces are to be linked, and plugs in the case where tubular pieces must be linked. The plugs may have slots and bores for the introduction of an expanding device. Advantageously, the bores penetrate the hinge, too. The plugs may thus be shaped like dowels, because for certain applications such a shape and/or a porous structure thereof may be advantageous, so that they fit especially well into the contours of the hollows where they are inserted by cutting or non-cutting shaping. A porous structure of the plug allows furthermore a microform-closing bond by adhesion or, in the case of medical use, by coalescence.

The hinge joint of the invention can be applied in all technological fields, and it is especially suitable for linking tubular elements. In this case, the dowel-like shape of its fixing elements and the lack of any axle pin or bolt is particularly advantageous, because the dowel-shaped plugs can be expanded and the hinge joint thus adjusted and fastened at any time, that is, even after having linked the two halves of the hinge. This property, as well as the porous structure of the plugs and the possibility of providing a flat design in the direction of the axis allow the hinge joint of the invention to be used as artificial joint for uniaxial articulations of man and animal.

The invention will be better understood by reference to the accompanying drawings, of which FIG. 1 represents a side view of the hinge joint in straight-angled position;

FIG. 2 shows an axial longitudinal section of the hinge joint;

FIG. 3 shows the item Z of FIG. 2 (guide ring in undercut groove);

FIG. 4 demonstrates the hinge joint mounted between two tubes and being in elbow position;

FIG. 5 represents the section V—V of FIG. 4 through the dowel-shaped plug in mounted state;

FIG. 6 represents the section VI—VI of FIG. 2.

In the Example illustrated by FIGS. 1 to 5 the halves of the hinge are linked with each other by two rings 3 and 4. The swivelling angle of the hinge joint is predetermined by the stop faces 5 and 6 and 7 and 8. The rings 3 and 4 are engaged in undercut grooves 9 and 10. The hinge joint is provided with two plugs 1 and 2 containing slots 11 and 12, which plugs serve as fixing elements and can be expanded like dowels by means of expanding elements 13, 14 being pressed into the bores 17, 18 of the plugs by means of tool 15 with grub screw 16. The grub screw 16 runs in the threads 19, 20, which may be tapped in advance or are formed by screwing in the tool 15. The channels 21, 22 in the hinge ensure adjustment and fixing of the hinge joint in undivided state. For various applications, especially in the medical field, it may be advantageous to cover the front faces of the hinge, for which purpose the rings 3 and 4 may be linked with covers 29 via bridges 28.

Both halves of the hinge are manufactured as a single molded article; the piece forming the hinge optionally having a prismatic or cylindrical shape. Subsequently, the molded article is cut for example by means of a punching tool, while taking into consideration the swivelling angle 25 and the position of the stops 5, 6, 7 and 8, so that the recesses 26 and 27 are thus formed also in this operation. Thereafter, the rings 3 and 4 are engaged in the undercut grooves 9 and 10, and the bores 17 and 18 for the expanding elements 13 and 14 are drilled, thus forming simultaneously the channels 21 and 22. The threads 19 and 20 for driving in the expanding elements 13 and 14 may be tapped by tool 15 in the mounting operation. The plugs 1 and 2 at the hinge halves can be slotted immediately before mounting by means of a suitable cutting device, while taking into consideration the shape of the recesses of the parts to be linked.

Suitable materials for the manufacture of the hinge joint are metals, plastics or, especially, pulverulent material capable of sintering, such as moldable plastics, synthetic resins, ceramic compositions or metals which should all be capable of being sintered.

The blank is shaped by pressing in a mold the powder capable of sintering in a defined manner, and subsequently heating it. In order to ensure a compact material in the area of the hinge and a porous one in the area of the fixing elements, the powder is compressed at a higher pressure in the first than in the latter area. When the powder of a partially crystalline plastic material is used, the heat treatment is carried out at a temperature above the crystallite melting point. Thus, the highly compressed powder is fused to form a compact material, while the powder grains in the area less pressed are linked together to form a porous material. The diverse material properties at determined places of the article are produced exclusively by a different compression of the powder; differing temperatures at the corresponding places of the mold are allowed, but not required.

What is claimed is:

1. A hinge joint comprising first and second hinge half elements, said elements having identical mirror image configurations; each hinge half element having a pair of angularly related stop surfaces meeting at an apex defining the pivot axis, the corresponding stop surfaces of each hinge half element being located to abut each other when the hinge half elements are pivoted about said pivot axis; said hinge half elements each having at least one arcuate groove formed therein defining a portion of a circle concentric with said axis; and an annular ring slidably received in said grooves and rotatably connecting said hinge half elements together.

2. A hinge joint as defined in claim 1 wherein said hinge half elements have opposed relatively flat surfaces extending transversely of said axis and an arcuate groove formed in each of said surfaces concentric with said axis; and an annular ring slidably received in each of said grooves.

3. A hinge joint as defined in claim 1 wherein the angle between said stop surfaces of the hinge half elements is selected such that at least 35% of the ring is supported in the grooves of the hinge half elements.

4. A hinge joint as defined in claim 1 wherein said grooves are undercut.

5. A hinge joint as defined in claim 1 wherein said hinge half elements each include means for securing the hinge half element to another object, said means being located at a radial position from said axis.

6. A hinge joint as defined in claim 5 wherein said means comprise radially extending plugs; said plugs each having a free end, a longitudinal bore formed through substantially its entire length, and a longitudinal slot in said free end whereby said plug may be expanded upon insertion of an expander pin in said bore to secure the plug in another object.

7. A hinge joint as defined in claims 5 or 6 wherein said securing means is formed of a micro-porous structure.

* * * * *